United States Patent [19]

Carlyle et al.

[11] 4,297,351

[45] Oct. 27, 1981

[54] METHOD OF MANUFACTURE AND USE OF IMPROVED 2β, 16β-PIPERIDINO ANDROSTANES

[75] Inventors: Ian C. Carlyle, Hamilton; Thomas Sleigh, Wishaw; David S. Savage, Glasgow, all of Scotland

[73] Assignee: Akzona Incorporated, Asheville, N.C.

[21] Appl. No.: 194,942

[22] Filed: Oct. 7, 1980

Related U.S. Application Data

[63] Continuation of Ser. No. 67,878, Aug. 20, 1979, Pat. No. 4,237,126.

[30] Foreign Application Priority Data

Sep. 5, 1978 [GB] United Kingdom ............... 35667/78

[51] Int. Cl.³ ............................................. A61K 31/58
[52] U.S. Cl. .................................. 424/241; 260/239.5
[58] Field of Search ...................... 260/239.5; 424/241

[56] References Cited

U.S. PATENT DOCUMENTS

| | | |
|---|---|---|
| 3,553,212 | 1/1971 | Hewett et al. .................... 260/239.5 |
| 3,872,091 | 3/1975 | Leslie et al. ..................... 260/239.5 |
| 4,101,545 | 7/1978 | Tuba et al. ....................... 260/239.5 |
| 4,110,326 | 8/1978 | Tuba et al. ....................... 260/239.5 |
| 4,177,190 | 12/1979 | Tuba et al. ..................... 260/239.5 |

FOREIGN PATENT DOCUMENTS

| | | |
|---|---|---|
| 2319370 | 8/1975 | France . |
| 1138605 | 1/1969 | United Kingdom ............. 260/239.5 |
| 1454749 | 11/1976 | United Kingdom ............. 260/239.5 |

OTHER PUBLICATIONS

W. R. Buckett et al., Pancuronium Bromide and Other Steroidal Neuromuscular Blocking Agents Containing Acetylcholine Fragments, J. Medicinal Chem. 16(10), at pp. 1116 to 1123 (1073).

*Primary Examiner*—Elbert L. Roberts
*Attorney, Agent, or Firm*—Robert H. Falk; Charles A. Wendel; Francis W. Young

[57] ABSTRACT

New and pharmacologically useful pharmaceutically acceptable acid addition salts are disclosed for the 16β-monoquaternary ammonium derivatives of either the 2β, 16β-bis-piperdino-3α, 17β-dihydroxy-5α-androstane 3α, 17β-di-lower aliphatic esters or the 2β, 16β-bis-piperidino-3α-hydroxy-5α-androstane-3α-lower aliphatic esters, which salts are surprisingly relatively stable in aqueous solutions, so that they provide stable aqueous injection preparations.

44 Claims, No Drawings

METHOD OF MANUFACTURE AND USE OF IMPROVED 2β, 16β-PIPERIDINO ANDROSTANES

This is a continuation of application Ser. No. 067,878 filed Aug. 20, 1979 now U.S. Pat. No. 4,237,126.

BACKGROUND OF THE INVENTION

1. Field of the Invention

The invention relates to the field of pharmacologically active 2β, 16β-bis-piperidino-androstanes, and more specifically, to the use of bis-quaternary ammonium compounds of derivatives of said androstanes as neuromuscular blocking agents.

2. Description of the Prior Art, and Other Information

From British Pat. No. 1,138,605, incorporated herein, (see also U.S. Pat. No. 3,553,212) it is known that certain bis-quaternary ammonium compounds of 2β,16β-bis-piperidino-3α,17β-dihydroxy-5α-androstane-3α,17β-diesters are highly active neuromuscular blocking agents.

A similar observation was made in Journal of Med. Chemistry 16, 1116, 1973, incorporated herein, but besides bis-quaternary ammonium compounds of 2β,16β,bis-piperidino-3α,17β-dihydroxy-5α-androstane-3α,17β-diesters, also 16-mono-quaternary ammonium compounds of these diesters are described to have the same order of potency as the corresponding bis-quaternary compounds.

16-Mono quaternary- as well as 2,16-bis quaternary ammonium compounds of 2β,16β-bis-piperidino-3α-hydroxy-5α-androstane-3α-esters are further known from the British Pat. No. 1,454,749, incorporated herein (see also U.S. Pat. No. 3,872,091).

It has been found that the 16-mono-quaternary ammonium derivatives of the said mono- and diesters in question turned out to be even more interesting compounds than the corresponding bis-quaternary ammonium compounds because of their quicker onset and shorter duration of action, which offer under most surgical conditions pronounced advantages, and because of their lack of cardiovascular side-effects.

However, in contrast to the bis-quaternary compounds, the 16-mono-quaternary ammonium compounds of 2β,16β-bis-piperidino-3α,17β-dihydroxy-5α-androstane 3α,17β-diesters and the corresponding 17β-unsubstituted 3α-mono-esters start to decompose almost immediately when dissolved in water and hence cannot be used in aqueous injection preparations.

Since neuromuscular blocking agents are mainly used in surgical treatments and are administered through injection, it would be a definite advance in the art to possess a stable aqueous injection preparation containing the 16-mono-quaternary ammonium compound of 2β,16β-bis-piperidino-3α,17β-dihydroxy-5α-androstane 3α,17β-diesters or of the corresponding 17β-unsubstituted-3α-mono-esters.

Surprisingly, it has now been found that the pharmaceutically acceptable acid addition salts of the 16β-mono-quaternary ammonium derivatives of either 2β,16β-bis-piperidino-3α,17β-dihydroxy-5α-androstane 3α,17β-di-lower aliphatic esters or 2β, 16β-bis-piperidino-3α-hydroxy-5α-androstane-3α-lower aliphatic esters are relatively stable in aqueous solutions to the extent that they can provide stable aqueous injection preparations.

Particularly preferred are the acid addition salts of compounds of the general formula (I):

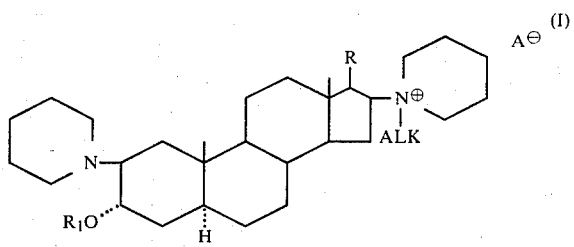

wherein:
(a) R is hydrogen or the moiety $-OR_2$;
(b) $R_1$ and $R_2$ each represent an unsubstituted acyl group derived from a lower aliphatic carboxylic acid of one to about six carbons;
(c) ALK is an unsubstituted alkyl, alkenyl or alkynyl group of one to four carbon atoms; and
(d) $A^{\ominus}$ represents a pharmaceutically acceptable organic or inorganic anion.

DESCRIPTION OF THE PREFERRED EMBODIMENTS

The acyl group in the definition of $R_1$ and $R_2$ is derived from lower aliphatic carboxylic acids of from one to about six carbons carbon atoms, for example, acetic acid, propionic acid, butyric acid, pentanoic acid, hexanoic acid, pivalic acid and iso-butyric acid; the acetyl group being a preferred moiety.

Examples of suitable ALK-groups in the compounds of formula I are methyl, ethyl, propyl, butyl, allyl, ethynyl and propargyl. The methyl group is especially preferred.

The anion ($A^{\ominus}$) used to neutralise the 16-quaternary ammonium cation in compound I may in principle be any pharmaceutically acceptable organic or inorganic anion known to those in the art. Preferred anions are methyl-sulphate, p-toluene-sulphonate and especially the halides such as chloride, bromide and iodide.

The acid addition salts according to the invention may in principle be derived from any pharmaceutically acceptable, suitable organic or inorganic acid known to those in the art. Preferably the acid itself is water-soluble. Examples of suitable inorganic acids are hydrochloric acid, hydrobromic acid, hydroiodic acid, nitric acid, sulphuric acid and phosphoric acid; examples of suitable organic acids are lower aliphatic mono, di- or tri-carboxylic acids, such as acetic acid, propionic acid, butyric acid, caproic acid, malonic acid, succinic acid, glutaric acid, maleic acid, fumaric acid, tartaric acid, malic acid, pyruvic acid, lactic acid and citric acid.

The acid addition salts of the invention are prepared in the usual manner known to those in the art by adding the acid in question to the 16-mono-quaternary ammonium derivative according to formula I in a suitable liquid.

A relatively stable, injectable, aqueous pharmaceutical preparation or composition of the 16-mono-quaternary ammonium derivative according to formula (I) can thus be obtained by dissolving the acid addition salt of the invention in water under aseptic conditions. It can also be obtained by combining a pharmaceutically acceptable acid with an aqueous solution of the 16-mono-quaternary ammonium derivative according to formula I under aseptic conditions, whereby the acid addition salt is formed in situ.

The pharmaceutical composition may further be stabilized, if desired, by the addition of a pharmaceutically acceptable buffer system, which buffers are generally in the range of about pH 3 to about pH 4.5, such as an acetic acid/sodium acetate buffer or a citric acid/sodium phosphate buffer. Where the acid addition salt used or prepared in situ, is the acetate or citrate, the quantity of acetic acid or citric acid in the buffer system may obviously be reduced or omitted, dependent on the concentration of the acid addition salt in the aqueous solution.

The aqueous pharmaceutical preparation may be administered directly, may be stored for some time, or may be lyophilised.

The new acid addition salts of the invention are administered in the same molar quantities or dosages as is known or described for the known 2,16-bis-quaternary ammonium derivatives of $2\beta,16\beta$-dipiperidino-$3\alpha,17$-dihydroxy-$5\alpha$-androstane $3\alpha,17\beta$-diesters.

Although the invention has been described with respect to the specific embodiments above, numerous variations and modifications will become evident to those skilled in the art without departing from the scope and spirit of the invention as described above, defined in the appended claims, and as shown in the following Examples.

EXAMPLE I $2\beta,16\beta$-dipiperidino-$5\alpha$-androstane-$3\alpha,17\beta$-diol diacetate $16\beta$N-methobromide hydrochloride A saturated solution of hydrogen chloride in dry ether (10 ml) was added dropwise to a stirred, cooled solution of $2\beta,16\beta$-dipiperidino-$5\alpha$-androstane-$3\alpha,17\beta$-diol diacetate $16\beta$N-methobromide (0.5 g) in dry methylene dichloride (10 ml), and the resulting solution evaporated to dryness in vacuo. The product was crystallised from acetone to afford $2\beta,16\beta$-di-piperidino-$5\alpha$-androstane-$3\alpha,17\beta$-diol diacetate $16\beta$N-methobromide hydrochloride as a white solid (0.39 g) m.p. 208°–212°.

$2\beta,16\beta$-dipiperidino-$5\alpha$-androstane-$3\alpha,17\beta$-diol $3\alpha$-propionate $17\beta$-acetate $16\beta$N-methobromide hydrochloride was similarly prepared and crystallised from acetone, m.p. 213°–222°.

In a similar manner may be prepared:
$2\beta,16\beta$-dipiperidino-$5\alpha$-androstane-$3\alpha$-ol $\quad$ $3\alpha$-acetate $16\beta$N-methobromide hydrochloride;
$2\beta,16\beta$-dipiperidino-$5\alpha$-androstane-$3\alpha$-ol $\quad$ $3\alpha$-acetate $16\beta$N-allylobromide hydrochloride; and
$2\beta,16\beta$-dipiperidino-$5\alpha$-androstane-$3\alpha$-ol $\quad$ $3\alpha$-acetate $16\beta$N-propargylobromide hydrochloride.

EXAMPLE II

Hydrobromide

A solution of hydrogen bromide (1.5 mol) in dry ether (0.66 ml) was added to a stirred, cooled solution of $2\beta,16\beta$-dipiperidino-$5\alpha$-androstane-$3\alpha$-$17\beta$-diol diacetate $16\beta$N-methobromide (0.5 g) in dry methylene dichloride (10.0 ml), and the resulting solution evaporated to dryness in vacuo to yield a pale yellow solid (0.58 g). The product was refluxed in acetone for 15 min., cooled, then filtered and dried to afford $2\beta,16\beta$-dipiperidino-$5\alpha$-androstane-$3\alpha,17\beta$-diol diacetate $16\beta$N-methobromide hydrobromide as an off-white solid (0.35 g), m.p. 226°–238° (decomp.).

$2\beta,16\beta$-dipiperidino-$5\alpha$-androstane-$3\alpha,17\beta$-diol $3\alpha$-butyrate $17\beta$-acetate $16\beta$N-methobromide hydrobromide was similarly prepared and crystallised from acetone, m.p. 216°–220°.

EXAMPLE III

Maleate

A solution of maleic acid (0.085 g, 1.0 mol) in acetone (5 ml) was added with stirring to a solution of $2\beta,16\beta$-dipiperidino-$5\alpha$-androstane-$3\alpha,17\beta$-diol diacetate $16\beta$N-methobromide (0.5 g) in dry methylene dichloride (10 ml), and the resulting mixture evaporated to dryness in vacuo. The product was slaked with ether, filtered and dried to afford $2\beta,16\beta$-dipiperidino-$5\alpha$-androstane-$3\alpha,17\beta$-diol diacetate $16\beta$N-methobromide maleate as a pale yellow solid (0.55 g), m.p. 139°–145°.

$2\beta,16\beta$-dipiperidino-$5\alpha$-androstane-$3\alpha,17\beta$-diol $3\alpha$-butyrate $17\beta$-acetate $16\beta$N-methobromide maleate was similarly prepared and crystallised from acetone, m.p. 208°–217°.

EXAMPLE IV

Citrate

A solution of citric acid (0.16 g, 1.0 mol) in acetone (5 ml) was added with stirring to a solution of $2\beta,16\beta$-dipiperidino-$5\alpha$-androstane-$3\alpha,17\beta$-diol diacetate $16\beta$N-methobromide (0.5 g) in dry methylene dichloride (10 ml) and the resulting mixture evaporated to dryness in vacuo. The product was slaked with ether, filtered and dried to afford $2\beta,16\beta$-dipiperidino-$5\alpha$-androstane-$3\alpha,17\beta$-diol diacetate $16\beta$N-methobromide citrate as a white solid (0.59 g), m.p. 130°–158°.

$2\beta,16\beta$-dipiperidino-$5\alpha$-androstane-$3\alpha,17\beta$-diol $3\alpha$-propionate $17\beta$-acetate $16\beta$N-methobromide citrate was similarly prepared as an off white solid, m.p. 138°–173°.

EXAMPLE V

Phosphate

A solution of ortho phosphoric acid (0.075 g, 1.0 mol) in dry ether (10 ml) was added with stirring to a solution of $2\beta,16\beta$-dipiperidino-$5\alpha$-androstane-$3\alpha,17\beta$-diol diacetate $16\beta$N-methobromide (0.5 g) in dry methylene dichloride (10 ml) and the resulting mixture evaporated to dryness in vacuo. The product was slaked with ether, filtered and dried to afford $2\beta,16\beta$-dipiperidino-$5\alpha$-androstane-$3\alpha,17\beta$-diol diacetate $16\beta$N-methobromide phosphate as a white solid (0.58 g), m.p. 206°–223°.

$2\beta,16\beta$-dipiperidino-$5\alpha$-androstane-$3\alpha,17\beta$-diol $3\alpha$-pivalate $17\beta$-acetate $16\beta$N-methobromide phosphate was similarly prepared as a white solid, m.p. 198°–207°.

EXAMPLE VI $2\beta,16\beta$-dipiperidino-$5\alpha$-androstane-$3\alpha,17\beta$-diol $3\alpha$-pivalate $17\beta$-acetate $16\beta$N-methobromide tartrate.

A solution of tartaric acid (0.108 g, 1.0 mol) in acetone (8 ml) was added with stirring to a solution of $2\beta,16\beta$-dipiperidino-$5\alpha$-androstane-$3\alpha,17\beta$-diol $3\alpha$-pivalate $17\beta$-acetate $16\beta$N-methobromide (0.5 g) in dry methylene dichloride (10 ml) and the resulting mixture evaporated to dryness in vacuo. The product was slaked with ether, filtered and dried to afford $2\beta,16\beta$-dipiperidino-$5\alpha$-androstane-$3\alpha,17\beta$-diol $3\alpha$-pivalate $17\beta$-acetate $16\beta$N-methobromide tartrate as a white solid (0.59 g), m.p. 163°–212°.

EXAMPLE VII

Stability in Water

Aqueous solutions of 10 mg/ml of

Compound "A": 2β,16β-dipiperidino-5α-androstane-3α,17β-diol diacetate 16βN-methobromide known to those in the art, and Compound "B": 2β,16β-piperidino-5α-androstane-3α,17β-diol diacetate 16βN-methobromide hydrochloride of the invention were prepared and kept at room temperature.

Samples (20 μg) were taken at intervals, spotted directly onto TLC plates and run against a freshly prepared solution of A. The TLC solvent systems used were:

(i) n-butanol:water (6:1) on Macherey-Nagel precoated ALOX 25 ® plates, and (ii) methanol:1M sodium acetate (1:1) on Merck & Co., Inc., (P.O. Box 2000, Rahway, N.J. 07065) Silica Gel 60 ® plates

| Day | Presence of "A" in The Solution | Presence of "B" in The Solution |
|---|---|---|
| 0 | 100 | 100 |
| 1 | 10 | 98–99 |
| 2 | 5–10 | 98–99 |
| 4 | 5–10 | 95–97 |
| 8 | 3–8 | 94–96 |
| 28 | not detectable | 92–94 |
| 43 | not detectable | 80–90 |

Aqueous solutions of 15 mg/ml were further prepared of:

the hydrochloride, hydrobromide, maleate, citrate and phosphate of 2β,16β-dipiperidino-5α-androstane-3α,17β-diol diacetate-16βN-methobromide;

the hydrochloride and citrate of 2β,16β-dipiperidino-5α-androstane-3α,17β-diol 3α-propionate 17β-acetate 16βN-methobromide;

the hydrobromide and maleate of 2β,16β-dipiperidino-5α-androstane-3α,17β-diol 3α-butyrate 17β-acetate 16βN-methobromide; and the phosphate and tartrate of 2β,16β-dipiperidino-5α-androstane-3α,17β-diol 3α-pivalate 17β-acetate 16βN-methobromide;

and examined by thin layer chromatography (TLC) over a period of 8 days. (System: methanol:sodium acetate 1M 1:1 on Merck Silica Gel 60 ® plates). Both hydrochlorides showed a decomposition of approximately 5%, the other salts less than 5%. In the same period a 10 mg/ml solution of "A" showed a decomposition of about 92–97%.

EXAMPLE VIII

Stability in plasma

Blank dog plasma solutions of 0.2 g/ml of

Compound "A": 2β,16β-dipiperidino-5α-androstane-3α,17β-diol diacetate 16βN-methobromide known to those in the art, and Compound "B": 2β,16β-piperidino-5α-androstane-3α,17β-diol diacetate 16βN-methobromide hydrochloride of the invention were prepared and kept at room temperature.

Samples (one ml) were taken at intervals (i.e. after 1.5 h, 4 h and 24 h) and processed as follows:

One ml portion of plasma was mixed with 1 ml phosphate buffer (pH = 6.5) and 100 μl of picric acid (0.05 M, pH = 6.5, adjusted with NaOH). Compound "A" or "B" and its possible hydrolysis products were extracted as ion pairs to a methylene chloride phase (2 ml) by gently shaking. The methylene chloride phase was evaporated to dryness under nitrogen at 40° C. The residue was redissolved in 50 μl MeOH/CH$_3$CN (1:1, v/v). An aliquot was injected into a HPLC system, employing a straight phase Lichrosorb Si 60 column (L=25 cm, i.d.=4.0 mm, d$_p$=10 μm) thermostatted with a water jacket at 45° C. The solvent consisted of MeOH, 0.05 M NH$_4$Cl and 1% NH$_4$OH, which was shaken ultrasonically before use during 30 minutes, the flow rate was 1 ml/min and the compounds were monitored by means of UV detection at 215 nm.

Results:

| Time (h) | Percentage of "A" in plasma | Percentage of "B" in plasma |
|---|---|---|
| 0 | 100 | 100 |
| 1.5 | 72 | 100 |
| 4 | 51 | 100 |
| 24 | 7 | 100 |

It is claimed as the invention:

1. A method for the preparation of a pharmaceutically acceptable acid addition salt of the 16β-mono-quaternary ammonium derivative of either a 3α,17β-di-lower aliphatic ester of 2β,16β-dipiperidino-3α,17β-dihydroxy-5α-androstane or a 3α-lower aliphatic ester of 2β,16β-dipiperidino-3α-hydroxy-5α-androstane comprising adding a pharmaceutically acceptable acid to the 16β-mono-quaternary ammonium derivative of either a 3α,17β-di-lower aliphatic ester of 2β,16β-dipiperidino-3α,17β-dihydroxy-5α-androstane or a 3α-lower aliphatic ester of 2β,16β-dipiperidino-3α-hydroxy-5α-androstane in a suitable solvent.

2. In the method for the administration of a neuromuscular blocking agent by injection to a surgical patient, the improvement which comprises using as said neuromuscular blocking agent an effective amount of a pharmaceutically acceptable acid addition salt of the 16β-mono-quaternary ammonium derivative of either a 3α,17α-di-lower aliphatic ester of 2β,16β-dipiperidino-3α,17β-dihydroxy-5α-androstane or a 3α-lower aliphatic ester of 2β,16β-dipiperidino-3α-hydroxy-5α-androstane.

3. The method of claim 1, wherein the acid addition salt is derived from one of the acids selected from the group consisting of hydrochloric acid, hydrobromic acid, hydroiodic acid, nitric acid, sulphuric acid, phosphoric acid, acetic acid, propionic acid, butyric acid, caproic acid, malonic acid, succinic acid, glutaric acid, maleic acid, fumaric acid, tartaric acid, malic acid, pyruvic acid, lactic acid, and citric acid.

4. The method of claim 1, wherein said acid addition salt is an acid addition salt of a compound of the formula

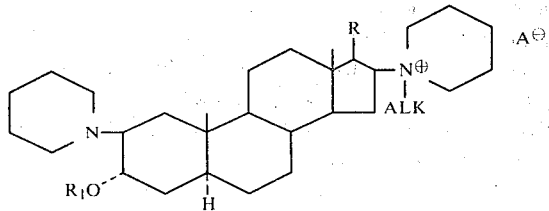

wherein:
(a) Represents H or the moiety —OR$_2$;
(b) R$_1$ and R$_2$ each represent an unsubstituted acyl group derived from a lower aliphatic carboxylic acid of one to about six carbons;
(c) ALK is an alkyl, alkenyl or alkynyl group of one to about four carbon atoms; and
(d) A$^\ominus$ represents a pharmaceutically acceptable organic or inorganic anion.

5. The method of claim 4, wherein at least one of R$_1$ and R$_2$ is acetyl.

6. The method of claim 5, wherein A$^\ominus$ is selected from the group consisting of methyl sulfate, p-toluene sulfonate, chloride, bromide, and iodide.

7. The method of claim 4, wherein ALK is methyl.

8. The method of claim 1, wherein the acid addition salt is 2β,16β-dipiperidino-5α-androstane-3α,17β-diol diacetate 16βN-methobromide hydrochloride.

9. The method of claim 1, wherein the acid addition salt is 2β,16β-dipiperidino-5α-androstane-3α,17β-diol 3α-proprionate 17β-acetate 16βN-methobromide hydrochloride.

10. The method of claim 1, wherein the acid addition salt is 2β,16β-dipiperidino-5α-androstane-3α-ol 3α-acetate 16βN-methobromide hydrochloride.

11. The method of claim 1, wherein the acid addition salt is 2β,16β-dipiperidino-5α-androstane-3α-ol 3α-acetate 16βN-allylobromide hydrochloride.

12. The method of claim 1, wherein the acid addition salt is 2β,16β-dipiperidino-5α-androstane-3α-ol 3α-acetate 16βN-propargylobromide hydrochloride.

13. The method of claim 1, wherein the acid addition salt is 2β,16β-dipiperidino-5α-androstane 3α,17β-diol diacetate 16βN-methobromide hydrobromide.

14. The method of claim 1, wherein the acid addition salt is 2β,16β-dipiperidino-5α-androstane-3α,17β-diol 3α-butyrate 17β-acetate 16βN-methobromide hydrobromide.

15. The method of claim 1, wherein the acid addition salt is 2β,16β-dipiperidino-5α-androstane-3α,17β-diol diacetate 16βN-methobromide maleate.

16. The method of claim 1, wherein the acid addition salt is 2β,16β-dipiperidino-5α-androstane-3α,17β-diol, 3α-butyrate 17β-acetate 16βN-methobromide maleate.

17. The method of claim 1, wherein the acid addition salt is 2β,16β-dipiperidino-5α-androstane-3α,17β-diol diacetate 16βN-methobromide citrate.

18. The method of claim 1, wherein the acid addition salt is 2β,16β-dipiperidino-5α-androstane-3α,17β-diol 3α-propionate 17β-acetate 16βN-methobromide citrate.

19. The method of claim 1, wherein the acid addition salt is 2β,16β-dipiperidino-5α-androstane-3α,17β-diol diacetate 16βN-methobromide phosphate.

20. The method of claim 1, wherein the acid addition salt is 2β,16β-dipiperidino-5α-androstane-3α,17β-diol 3α pivalate 17β-acetate 16βN-methobromide phosphate.

21. The method of claim 1, wherein the acid addition salt is 2β,16β-dipiperidino-5α-androstane-3α,17β-diol 3α pivalate 17β-acetate 16βN-methobromide tartrate.

22. The method of claim 1, wherein said acid addition salt has the formula:

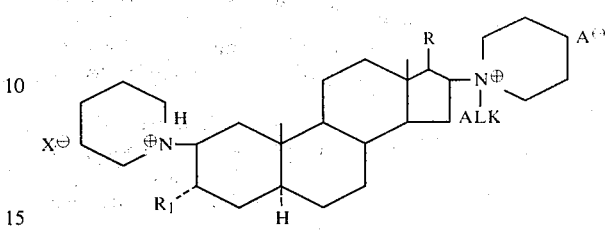

(a) R represents H or the moiety —OR$_2$;
(b) R$_1$ and R$_2$ each represent an unsubstituted acyl group derived from a lower aliphatic carboxylic acid of one to about six carbons;
(c) ALK is an alkyl, alkenyl, or alkynyl group of one to about four carbon atoms; and
(d) A$^\ominus$ and X$^\ominus$ each represents a pharmaceutically acceptable organic or inorganic anion.

23. The method of claim 22 wherein X$^\ominus$ and A$^\ominus$ are identical.

24. The method of claim 2, wherein the acid addition salt is derived from one of the acids selected from the group consisting of hydrochloric acid, hydrobromic acid, hydroiodic acid, nitric acid, sulphuric acid, phosphoric acid, acetic acid, propionic acid, butyric acid, caproic acid, malonic acid, succinic acid, glutaric acid, maleic acid, fumaric acid, tartaric acid, malic acid, pyruvic acid, lactic acid, and citric acid.

25. The method of claim 2, wherein said acid addition salt is an acid addition salt of a compound of the formula

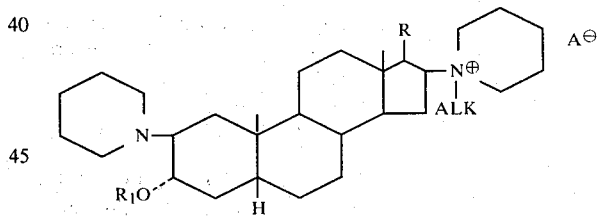

wherein:
(a) R represents H or the moiety —OR$_2$;
(b) R$_1$ and R$_2$ each represent an unsubstituted acyl group derived from a lower aliphatic carboxylic acid of one to about six carbons;
(c) ALK is an alkyl, alkenyl or alkynyl group of one to about four carbon atoms; and
(d) A$^\ominus$ represents a pharmaceutically acceptable organic or inorganic anion.

26. The method of claim 25, wherein at least one of R$_1$ and R$_2$ is acetyl.

27. The method of claim 26, wherein A$^\ominus$ is selected from the group consisting of methyl sulfate, p-toluene sulfonate, chloride, bromide, and iodide.

28. The method of claim 25, wherein ALK is methyl.

29. The method of claim 2, wherein the acid addition salt is 2β,16β-dipiperidino-5α-androstane-3α,17β-diol diacetate 16βN-methobromide hydrochloride.

30. The method of claim 2, wherein the acid addition salt is 2β,16β-dipiperidino-5α-androstane-3α,17β-diol 3α-proprionate 17β-acetate 16βN-methobromide hydrochloride.

31. The method of claim 2, wherein the acid addition salt is 2β,16β-dipiperidino-5α-androstane-3α-ol 3α-acetate 16βN-methobromide hydrochloride.

32. The method of claim 2, wherein the acid addition salt is 2β,16β-dipiperidino-5α-androstane-3α-ol 3α-acetate 16βN-allylobromide hydrochloride.

33. The method of claim 2, wherein the acid addition salt is 2β,16β-dipiperidino-5α-androstane-3α-ol 3α-acetate 16βN-propargylobromide hydrochloride.

34. The method of claim 2, wherein the acid addition salt is 2β,16β-dipiperidino-5α-androstane 3α,17β-diol diacetate 16βN-methobromide hydrobromide.

35. The method of claim 2, wherein the acid addition salt is 2β,16β-dipiperidino-5α-androstane-3α,17β-diol 3α-butyrate 17β-acetate 16βN-methobromide hydrobromide.

36. The method of claim 2, wherein the acid addition salt is 2β,16β-dipiperidino-5α-androstane-3α,17β-diol diacetate 16βN-methobromide maleate.

37. The method of claim 2, wherein the acid addition salt is 2β,16β-dipiperidino-5α-androstane-3α,17β-diol 3α-butyrate 17β-acetate 16βN-methobromide maleate.

38. The method of claim 2, wherein the acid addition salt is 2β,16β-dipiperidino-5α-androstane-3α,17β-diol diacetate 16βN-methobromide citrate.

39. The method of claim 2, wherein the acid addition salt is 2β,16β-dipiperidino-5α-androstane-3α,17β-diol 3α-propionate 17β-acetate 16βN-methobromide citrate.

40. The method of claim 2, wherein the acid addition salt is 2β,16β-dipiperidino-5α-androstane-3α,17β-diol diacetate 16βN-methobromide phosphate.

41. The method of claim 2, wherein the acid addition salt is 2β,16β-dipiperidino-5α-androstane-3α,17β-diol 3α pivalate 17β-acetate 16βN-methobromide phosphate.

42. The method of claim 2, wherein the acid addition salt is 2β,16β-dipiperidino-5α-androstane-3α,17β-diol 3α pivalate 17β-acetate 16βN-methobromide tartrate.

43. The method of claim 2, wherein said acid addition salt has the formula

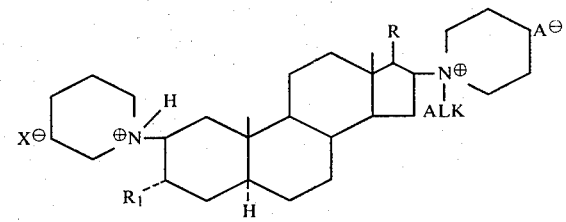

wherein:
(a) R represents H or the moiety $-OR_2$;
(b) $R_1$ and $R_2$ each represent an unsubstituted acyl group derived from a lower aliphatic carboxylic acid of one to about six carbons;
(c) ALK is an alkyl, alkenyl, or alkynyl group of one to about four carbon atoms; and
(d) $A^{\ominus}$ and $X^{\ominus}$ each represents a pharmaceutically acceptable organic or inorganic anion.

44. The method of claim 43 wherein $X^{\ominus}$ and $A^{\ominus}$ are identical.

* * * * *

UNITED STATES PATENT AND TRADEMARK OFFICE
CERTIFICATE OF CORRECTION

PATENT NO. : 4,297,351
DATED : October 27, 1981
INVENTOR(S) : Ian C. Carlyle et al.

It is certified that error appears in the above—identified patent and that said Letters Patent is hereby corrected as shown below:

The term of this patent subseauent to December 2, 1997 has been disclaimed.

*Signed and Sealed this*

*Twelfth* Day of *January 1982*

[SEAL]

Attest:

GERALD J. MOSSINGHOFF

*Attesting Officer*     *Commissioner of Patents and Trademarks*